US008382972B2

(12) United States Patent
    Arimoto

(10) Patent No.: US 8,382,972 B2
(45) Date of Patent: *Feb. 26, 2013

(54) METHOD FOR QUANTIFYING A CHEMICAL SUBSTANCE WITH SUBSTITUTIONAL STRIPPING VOLTAMMETRY AND A SENSOR CHIP USED THEREFOR

(75) Inventor: Satoshi Arimoto, Shiga (JP)

(73) Assignee: Panasonic Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/315,478

(22) Filed: Dec. 9, 2011

(65) Prior Publication Data

US 2012/0073991 A1   Mar. 29, 2012

Related U.S. Application Data

(63) Continuation of application No. PCT/JP2011/001774, filed on Mar. 25, 2011.

(30) Foreign Application Priority Data

Sep. 27, 2010   (JP) ................................ 2010-214895

(51) Int. Cl.
    G01N 27/416    (2006.01)
    G01N 27/327    (2006.01)
(52) U.S. Cl. ..................... 205/777.5; 205/775; 204/434; 204/403.01; 204/402
(58) Field of Classification Search .................. 204/400, 204/402, 403.01, 434; 205/775, 777.5
    See application file for complete search history.

(56) References Cited

U.S. PATENT DOCUMENTS

| 7,758,735 B2* | 7/2010 | Hengstenberg et al. | 204/412 |
| 7,842,637 B2* | 11/2010 | Ebron et al. | 502/160 |
| 8,211,283 B2* | 7/2012 | Kendig et al. | 204/435 |
| 2003/0188977 A1 | 10/2003 | Chalyt et al. | |

FOREIGN PATENT DOCUMENTS

| EP | 0 569 908 A2 | 11/1993 |
| JP | 3289059 | 3/2002 |
| JP | 2005-521883 | 7/2005 |

OTHER PUBLICATIONS

Senda et al, Collection of Czechoslovak Chemical Communicatios, 66, pp. 445-455, 2001.*
International Search Report issued in International Patent Application No. PCT/JP2011/001774 dated May 31, 2011.

* cited by examiner

*Primary Examiner* — Keith Hendricks
*Assistant Examiner* — Susan D Leong
(74) *Attorney, Agent, or Firm* — McDermott Will & Emery LLP

(57) ABSTRACT

The evaporation of the stripping liquid 6 changes the concentration of the standard electrolyte. This causes the quantification accuracy of the chemical substance to be lowered.
In order to solve the above problem, this invention provides a method for quantifying a chemical substance contained in a sample solution, characterized by the following stripping gel. The stripping gel covers the stripping electrode, and contains a standard electrolyte and an ionic liquid; however, the stripping gel contains no water.
Furthermore, the ionic liquid is hydrophobic and nonvolatile, and the standard electrolyte is consisted of the anion and a metallic ion.

13 Claims, 4 Drawing Sheets

METHOD FOR QUANTIFYING A CHEMICAL SUBSTANCE WITH SUBSTITUTIONAL STRIPPING VOLTAMMETRY AND A SENSOR CHIP USED THEREFOR

RELATED APPLICATIONS

This is a continuation of PCT International Application PCT/JP2011/001774, filed on Mar. 25, 2011, which in turn claims the benefit of Japanese Application No. 2010-214895, filed on Sep. 27, 2010. The disclosures of these applications including the specifications, the drawings, and the claims are hereby incorporated by reference in their entirety.

BACKGROUND OF THE INVENTION

1. Field of the Invention

This invention relates to a method for quantifying a chemical substance with substitutional stripping voltammetry and a sensor chip used therefor.

2. Description of the Background Art

Patent Document 1 discloses substitutional stripping voltammetry. The substitutional stripping voltammetry allows a chemical substance contained in a solution to be electro-chemically quantified with high sensitivity.

FIG. 1 shows the system for the substitutional stripping voltammetry disclosed in the Patent Document 1.

The system comprises a pair of comb-shaped working electrodes 1, a stripping electrode 2, a reference electrode 3, a counter electrode 4, a solution 5, a stripping liquid 6, a salt bridge 7, an ion conductor 8, a potentiostat 9, a recorder 10, and a switch box 11.

The solution 5 contains a chemical substance to be quantified and an oxidation-reduction substance. The stripping liquid 6 contains a standard electrolyte and a support electrolyte.

FIG. 2 shows a sensor chip 101*a* employed for the substitutional stripping voltammetry disclosed in the Patent Document 1.

The sensor chip 101*a* comprises a plurality of electrodes 2 to 4 on the surface thereof. Furthermore, the container 64 covers the surface of the sensor chip 101*a*. The container 64 comprises a first penetrated opening 64*a* and a second penetrated opening 64*b*. The solution 5 and the stripping liquid 6 are supplied to the first penetrated opening 64*a* and the second penetrated opening 64*b*, respectively.

CITATION LIST

Patent Literature

[PTL 1] Japanese Patent Publication No. 3289059B.

SUMMARY OF THE INVENTION

Technical Problem

The evaporation of the stripping liquid 6 changes the concentration of the standard electrolyte. This causes the quantification accuracy of the chemical substance to be lowered.

The purpose of the invention is to provide a method for quantifying a chemical substance with high accuracy using substitutional stripping voltammetry and a sensor chip used therefor.

Solution to Problem

The following items [1] to [13] solve the above problem(s).
[1]: A method for quantifying a chemical substance contained in a sample solution, comprising the following steps (a) to (e):
 a step (a) of preparing a sensor chip (300), wherein,
  the sensor chip comprises a substrate (30), a pair of working electrodes (31*a*/31*b*), a counter electrode (33), a stripping electrode (34), and a stripping gel (35),
  the pair of working electrodes (31*a*/31*b*) is composed of a first working electrode (31*a*) and a second working electrode (31*b*),
  the surface of the stripping electrode (34) comprises gold, platinum, or glassy carbon,
  the stripping gel (35) covers the stripping electrode (34),
  the stripping gel (35) does not cover the pair of the working electrodes (31*a*/31*b*) or the counter electrode (33),
  the stripping gel (35) contains a standard electrolyte and an ionic liquid,
  the stripping gel (35) contains no water,
  the ionic liquid is hydrophobic and nonvolatile,
  the ionic liquid is consisted of a cation and an anion,
  the standard electrolyte is consisted of the anion and a metallic ion,
 a step (b) of supplying the sample solution to the surface of the sensor chip to cover the surface with the sample solution, wherein,
  the sample solution contains the chemical substance and an oxidation-reduction substance or contains the chemical substance modified with an oxidation-reduction substance,
 a step (c) of applying a potential to the first working electrode (31*a*) with potentiostat, and connecting the second working electrode (31*b*) to the stripping electrode (34) to generate reactions represented by the following formulas (I) to (III) in the respective surface of the first working electrode (31*a*), the second working electrode (31*b*), and the stripping electrode (34), respectively,
  the first working electrode (31*a*):

[Chem. 1]

$$\begin{bmatrix} \text{the} \\ \text{oxidation-} \\ \text{reduction} \\ \text{substance} \end{bmatrix}^{(n+m)} + m\,e^{\ominus} \longrightarrow \begin{bmatrix} \text{the} \\ \text{oxidation-} \\ \text{reduction} \\ \text{substance} \end{bmatrix}^{n} \quad \text{(I)}$$

(oxidant) (reductant)

(wherein, n represents an integer, and m represents a positive integer.)
 the second working electrode (31*b*):

[Chem. 2]

$$\begin{bmatrix} \text{the} \\ \text{oxidation-} \\ \text{reduction} \\ \text{substance} \end{bmatrix}^{n} \longrightarrow \begin{bmatrix} \text{the} \\ \text{oxidation-} \\ \text{reduction} \\ \text{substance} \end{bmatrix}^{(n+m)} + m\,e^{\ominus} \quad \text{(II)}$$

(reductant) (oxidant)

(wherein, n represents an integer, and m represents a positive integer.)
 the stripping electrode (34)

[Chem. 3]

$$M^{s\oplus} + se^{\ominus} \rightarrow M\downarrow \quad \text{(III)}$$

(wherein, M represents a metallic elements, and s represents a positive integer.)

wherein, the metal is deposited on the surface of the stripping electrode (34), a step (d) of applying a potential to the stripping electrode (34) in a condition where no potential is applied to either the first working electrode (31a) or the second working electrode (31b) to measure a current flowing through the stripping electrode (34), a step (e) of calculating the concentration of the oxidation-reduction substance (oxidant) to quantify the chemical substance on the basis of the calculated concentration.

[2]: A method according to above item [1], wherein,
the sensor chip (300) further comprises a cover (37) with an inlet (36),
a space is formed between the cover (37) and the sensor chip (300),
in the step (b), the sample solution is supplied through the inlet (36) to the surface of the sensor chip (300).

[3]: A method according to above item [2], wherein,
the sensor chip (300) further comprises an air vent (38),
in the step (b), the air which has filled the space is drained through the air vent (38).

[4]: A method according to above item [2], wherein,
after the step (b), the space is filled with the sample solution.

[5]: A method according to above item [1], wherein,
the cation and the anion are selected from the following groups (I) and (II), respectively:
Group (I): a cation represented by the following formula IV-(1) to IV-(6).

[Chem. 4]

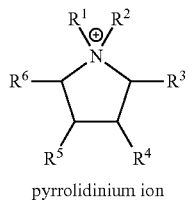

imidazolium ion
IV-(1)

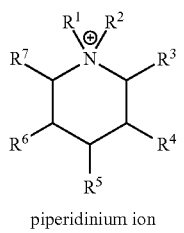

isoquinolium ion
IV-(2)

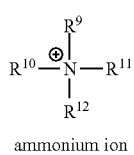

pyridinium ion
IV-(3)

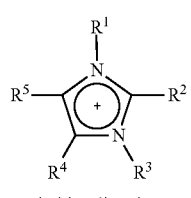

pyrrolidinium ion
IV-(4)

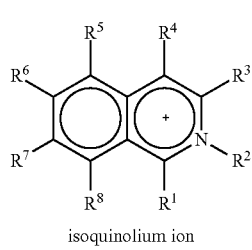

piperidinium ion
IV-(5)

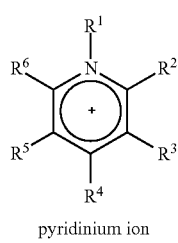

ammonium ion
IV-(6)

(wherein, $R^1$, $R^2$, $R^3$, $R^4$, $R^5$, $R^6$, $R^7$, and $R^8$ are the same as or different from each other, and represent hydrogen atom, a straight or branched alkyl group which may contain heteroatom, an aralkyl group, or an aryl group, and $R^9$, $R^{10}$, $R^{11}$, an $R^{12}$ are the same as or different from each other, and represent a straight or branched alkyl group which may contain heteroatom, an aralkyl group, or an aryl group.)

Group (II): an anion represented by the following formula V-(1) or V-(2).

[Chem. 5]

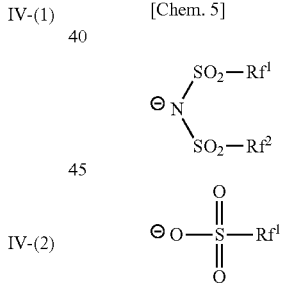

V-(1)

V-(2)

(wherein, $Rf^1$ and $Rf^2$ are the same as or different from each other, and represent a perfluoroalkyl group having carbon number of 1 to 4.)

[6]: A method according to above item [1], wherein,
the ionic liquid is selected from the followings:
1,3-Dimethylimidazolium bis(trifluoromethanesulfonyl)imide,
1-Ethyl-3-methylimidazolium bis(trifluoromethanesulfonyl)imide,
1-Ethyl-3-methylimidazolium triflate,
1-Ethyl-3-methylimidazolium bis(pentafluoroethanesulfonyl)imide,
1,3-Diethylimidazolium bis(trifluoromethanesulfonyl)imide,
1,3-Diethylimidazolium triflate,
1-Butyl-3-ethylimidazolium triflate, 1,2-Dimethyl-3-ethylimidazolium bis(trifluoromethanesulfonyl)imide,
1-Butyl-3-methylimidazolium bis(trifluoromethanesulfonyl)imide,
1-Butyl-3-methylimidazolium triflate,
1-isoPropyl-3-methylimidazolium bis(trifluoromethanesulfonyl)imide,
1,2-Dimethyl-3-propyllimidazolium bis(trifluoromethanesulfonyl)imide,
N,N-propylmethylpyrrolidinium bis(trifluoromethanesulfonyl)imide,
Propyltrimethyammonium bis(trifluoromethanesulfonyl)imide,
N,N-methylpropylpiperidinium bis(trifluoromethanesulfonyl)imide, and
N-butylpyridinium bis(trifluoromethanesulfonyl)imide.

[7]: A method according to above item [1], wherein,
the metallic ion is silver ion or copper ion (II).

[8]: A sensor chip for a substitutional stripping voltammetry, comprising:
a substrate (30),
a pair of working electrodes (31a/31b),
a counter electrode (33),
a stripping electrode (34), and
a stripping gel (35), wherein
the pair of working electrodes (31a/31b) is composed of a first working electrode (31a) and a second working electrode (31b),
the surface of the stripping electrode (34) comprises gold, platinum, or glassy carbon,
the stripping gel (35) covers the stripping electrode (34),
the stripping gel (35) does not cover the pair of the working electrodes (31a/31b) or the counter electrode (33),
the stripping gel (35) contains a standard electrolyte and an ionic liquid,
the ionic liquid is hydrophobic,
the ionic liquid is consisted of a cation and an anion,
the standard electrolyte is consisted of the anion and a metallic ion.

[9]: A sensor chip according to above item [8], wherein,
the sensor chip (300) further comprises a cover (37) with an inlet (36),
a space is formed between the cover (37) and the sensor chip (300).

[10]: A sensor chip according to above item [9], wherein, the sensor chip (300) further comprises an air vent (38).

[11]: A sensor chip according to above item [8], wherein,
the cation and the anion are selected from the following groups (I) and (II), respectively:
Group (I): a cation represented by the following formula IV-(1) to IV-(6).

[Chem. 4]

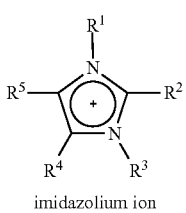

imidazolium ion

IV-(1)

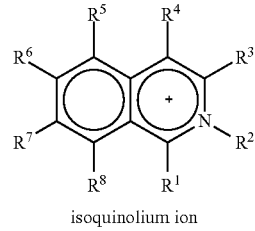

isoquinolium ion

IV-(2)

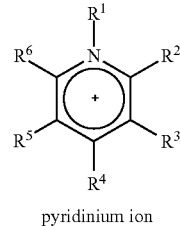

pyridinium ion

IV-(3)

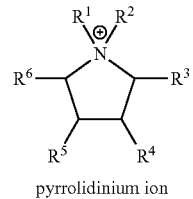

pyrrolidinium ion

IV-(4)

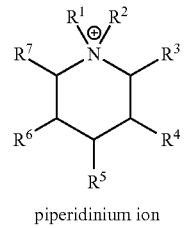

piperidinium ion

IV-(5)

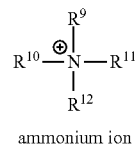

ammonium ion

IV-(6)

(wherein, $R^1$, $R^2$, $R^3$, $R^4$, $R^5$, $R^6$, $R^7$, and $R^8$ are the same as or different from each other, and represent hydrogen atom, a straight or branched alkyl group which may contain heteroatom, an aralkyl group, or an aryl group, and $R^9$, $R^{10}$, $R^{11}$, and $R^{12}$ are the same as or different from each other, and represent a straight or branched alkyl group which may contain heteroatom, an aralkyl group, or an aryl group.)

Group (II): an anion represented by the following formula V-(1) or V-(2).

[Chem. 5]

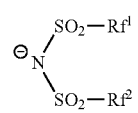

V-(1)

-continued

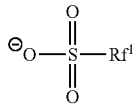
V-(2)

(wherein, Rf$^4$ and Rf$^2$ are the same as or different from each other, and represent a perfluoroalkyl group having carbon number of 1 to 4.)

[12]: A sensor chip according to above item [8], wherein, the ionic liquid is selected from the followings:
1,3-Dimethylimidazolium bis(trifluoromethanesulfonyl) imide,
1-Ethyl-3-methylimidazolium bis(trifluoromethanesulfonyl) imide,
1-Ethyl-3-methylimidazolium triflate,
1-Ethyl-3-methylimidazolium bis(pentafluoroethanesulfonyl)imide,
1,3-Diethylimidazolium bis(trifluoromethanesulfonyl) imide,
1,3-Diethylimidazolium triflate,
1-Butyl-3-ethylimidazolium triflate,
1,2-Dimethyl-3-ethylimidazolium bis(trifluoromethanesulfonyl)imide,
1-Butyl-3-methylimidazolium bis(trifluoromethanesulfonyl)imide,
1-Butyl-3-methylimidazolium triflate,
1-isoPropyl-3-methylimidazolium bis(trifluoromethanesulfonyl)imide,
1,2-Dimethyl-3-propyllimidazolium bis(trifluoromethanesulfonyl)imide,
N,N-Propylmethylpyrrolidinium bis(trifluoromethanesulfonyl)imide,
Propyltrimethyammonium bis(trifluoromethanesulfonyl) imide,
N,N-Methylpropylpiperidinium bis(trifluoromethanesulfonyl)imide, and
N-Butylpyridinium bis(trifluoromethanesulfonyl)imide.

[13]: A sensor chip according to above item [8], wherein, the metallic ion is silver ion or copper ion (II).

Advantageous Effects of Invention

The present invention provides a method for quantifying a chemical substance with high accuracy using substitutional stripping voltammetry and a sensor chip used therefor.

DESCRIPTION OF THE PREFERRED EMBODIMENTS

An embodiment of the present invention is described below with reference to FIG. 3 and FIG. 4.

(Step (a))

First, a sensor chip 300 is prepared.

Figure 1:
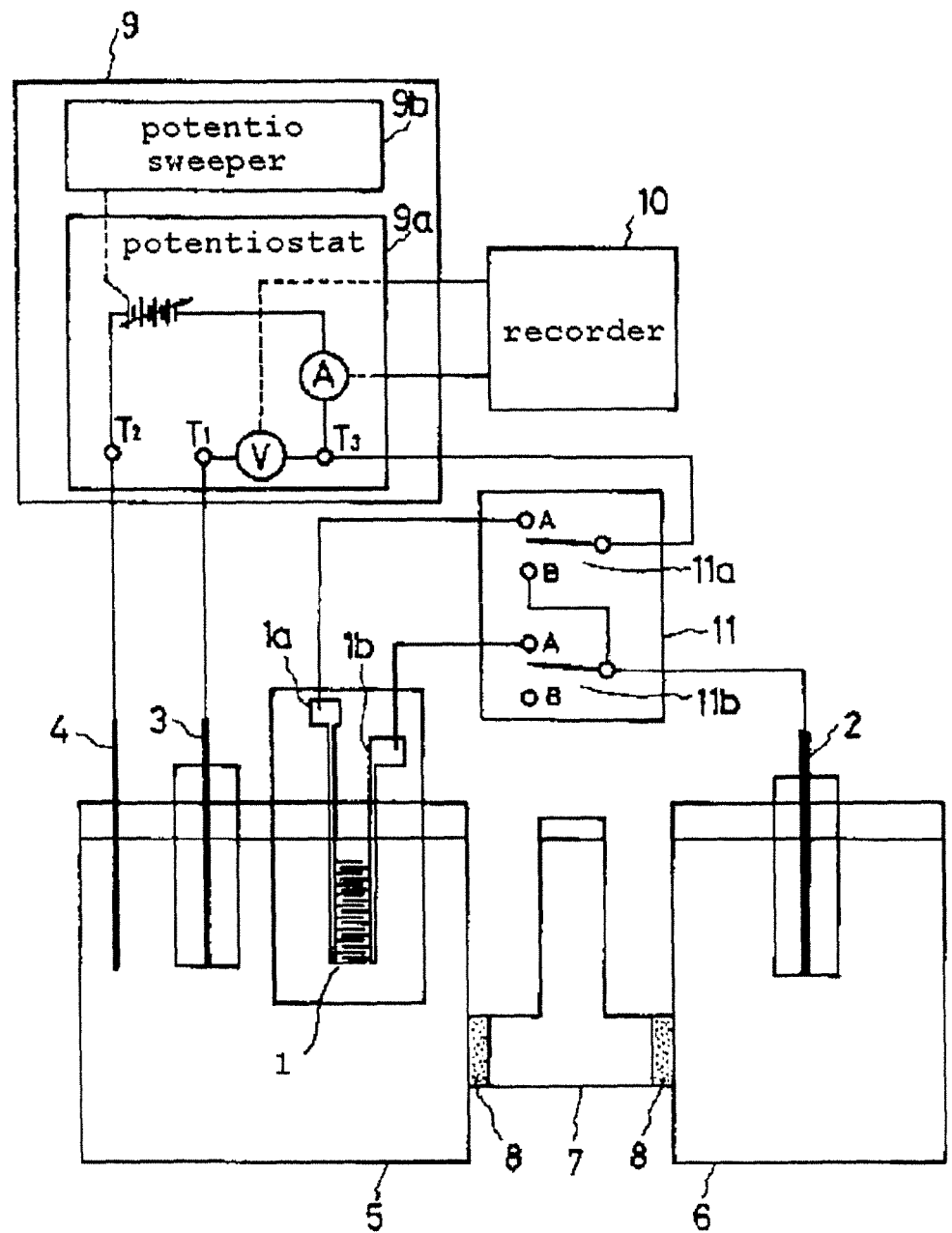
FIG. 1 shows the system for the substitutional stripping voltammetry disclosed in the Patent Document 1.
Figure 2:
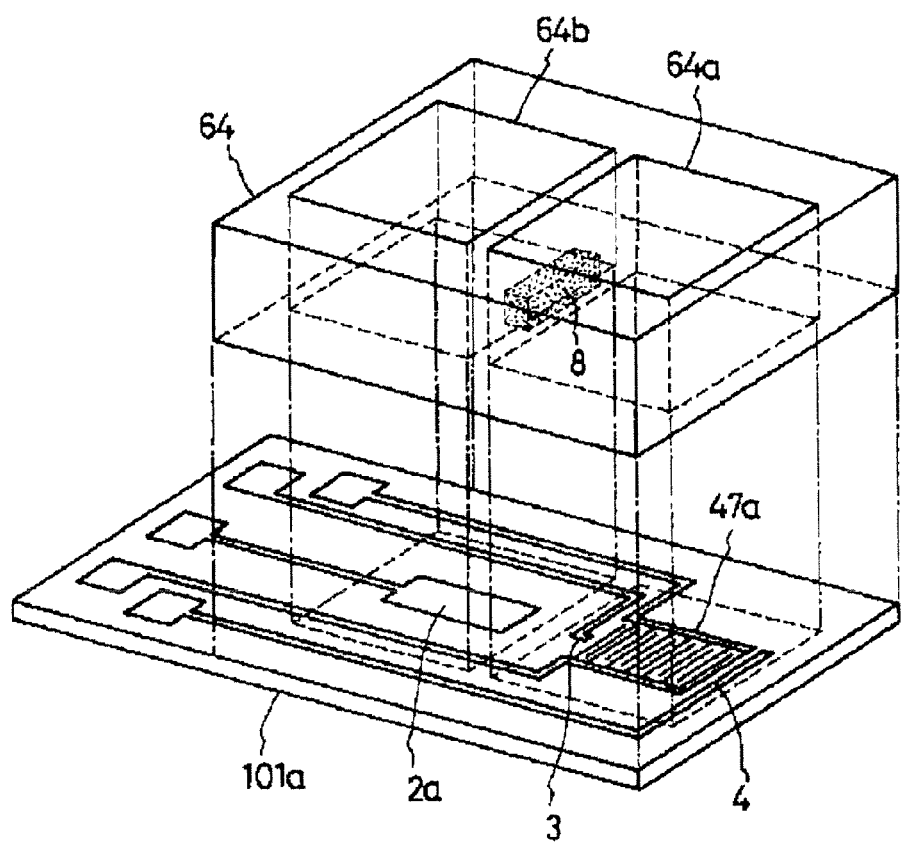
FIG. 2 shows a sensor chip 101a employed for the substitutional stripping voltammetry disclosed in the Patent Document 1.
Figure 3:
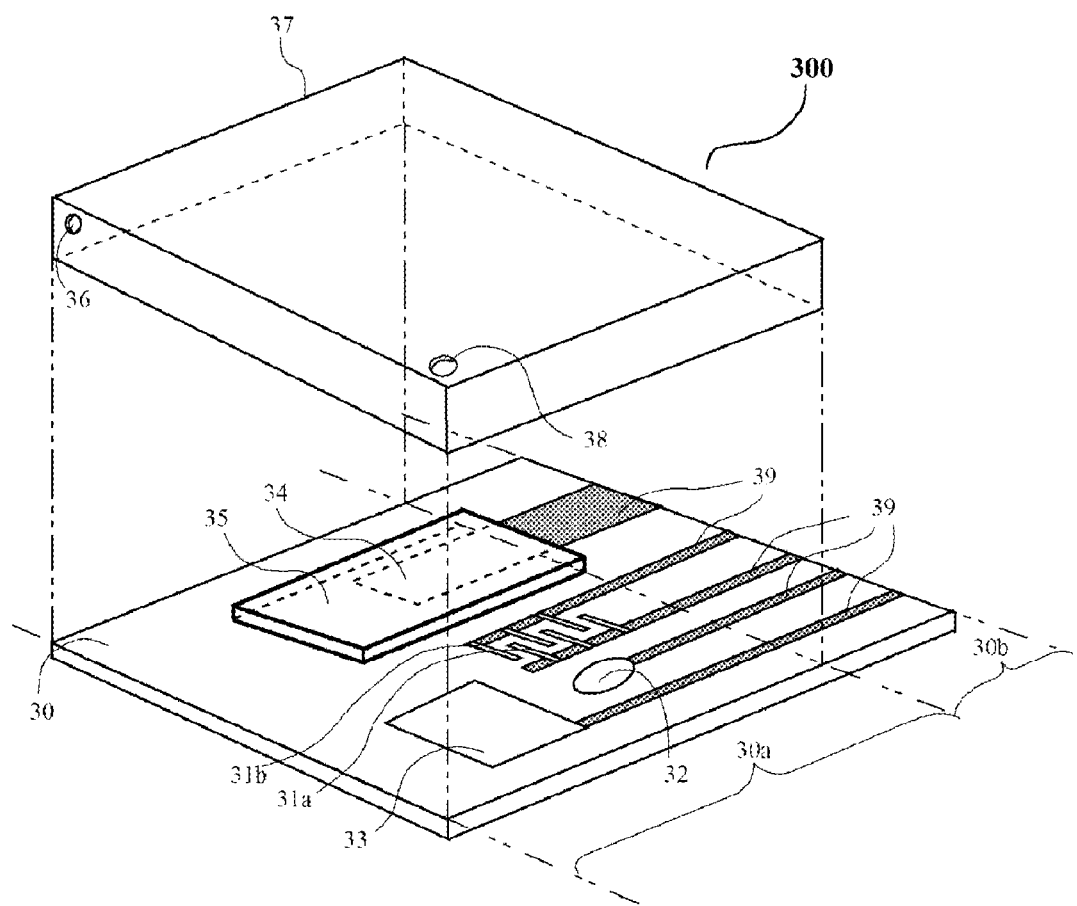
FIG. 3 shows the sensor chip 300 according to the embodiment 1.
Figure 4:
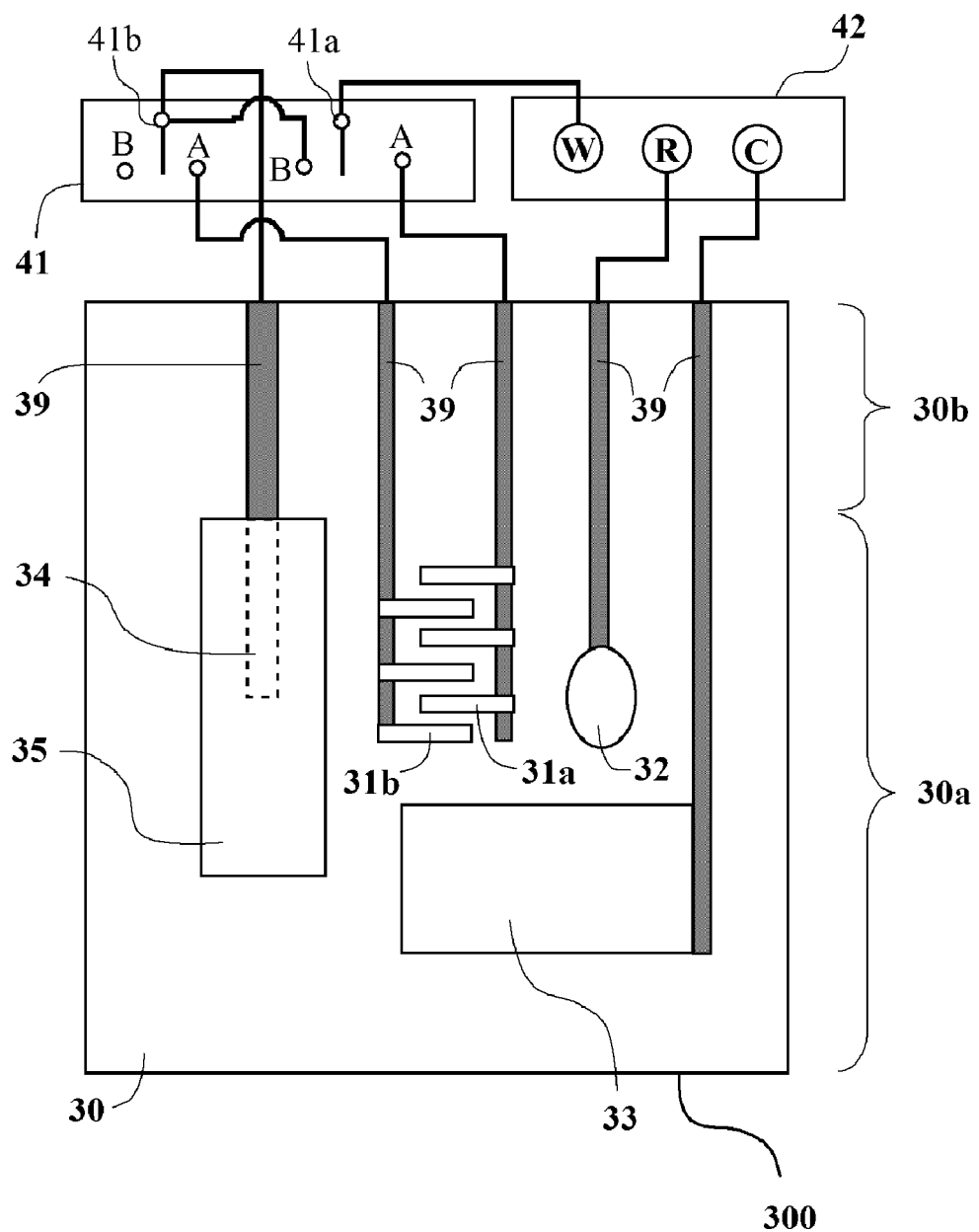
FIG. 4 schematically shows the sensor chip 300 which is connected to the potentiostat 42.

FIG. 3 shows the sensor chip 300 according to the embodiment 1. FIG. 4 schematically shows the sensor chip 300 which is connected to the potentiostat 42. The sensor chip 300 comprises a substrate 30, a pair of comb-shaped working electrodes 31a/31b, a reference electrode 32, a counter electrode 33, a stripping electrode 34, a striping gel 35, and a cover 37. The cover 37 is comprised optionally, and comprises an inlet 36 for injecting a sample solution and an air vent 38.

The pair of the comb-shaped working electrodes 31a/31b is composed of a first working electrode 31a and a second working electrode 31b.

The reference electrode 32 is comprised optionally. In light of high accuracy of the quantification, it is preferred that the sensor chip 300 comprises the reference electrode 32.

The substrate 30 comprises an electrode region 30a and a connection region 30b. The cover 37 covers the electrode region 30a on the quantification of the chemical substance, whereas the cover 37 does not cover the connection region 30b.

The pair of comb-shaped electrodes 31a/31b, the reference electrode 32, the counter electrode 33, and the stripping electrode 34 are formed in the electrode region 30a. Each of these electrodes comprises a lead wire(s) 39. All the lead wires 39 are not electrically connect to each other. In the electrode region 30a, they are covered with an insulator film (not shown), which prevents them from coming into contact with the sample solution. All the terminals of the lead wires 39 are extended into the connection region 30b, which is inserted into the connector (not shown) of the potentiostat 42 shown in FIG. 4.

An example of the shape of the substrate 30 is a rectangle, a square, and an ellipse. The surface of the substrate 30 comprises an insulator layer (not shown). Preferably, the surface of the substrate 30 is flat in light of formation of the electrodes.

The pair of comb-shaped electrodes 31a/31b are disposed anywhere in the electrode region 30a as long as they are not connected with the stripping gel 35 and other electrodes electrically. Preferably, they are disposed on the periphery of the center of the electrode region 30a. An example of the material of the pair of comb-shaped electrodes 31a/31b is gold, platinum, or glassy carbon in light of stability against electrochemical reactions. The pair of comb-shaped electrodes 31a/31b face each other and are engaged.

The reference electrode 32 is also disposed anywhere in the electrode region 30a. Preferably, it is disposed on the periphery of the pair of comb-shaped electrodes 31a/31b. On the electrochemical measuring, the reference electrode 32 has the constant potential. An example of the reference electrode 32 is a silver/silver chloride electrode.

The counter electrode 33 may be disposed anywhere in the electrode region 30a. The shape of the counter electrode 33 is not also limited. It is preferred that the area of the counter electrode 33 is approximately twenty to thirty times as large as the area of the pair of comb-shaped electrode 31a/31b and the area of the stripping electrode 34. An example of the material of the counter electrode 33 is gold, platinum, and glassy carbon in light of stability against electrochemical reactions similarly to the pair of comb-shaped electrodes 31a/31b.

An example of the material of the stripping electrode 34 is gold, platinum, and glassy carbon in light of stability against electrochemical reactions similarly to the pair of comb-shaped electrodes 31a/31b, and the counter electrode 33.

The stripping gel 35 covers the stripping electrode 34, which prevents the stripping electrode 34 from coming into contact with the sample solution. It is preferred that the stripping gel 35 is located on the periphery of the pair of comb-shaped electrodes 31a/31b to lower the resistance therebetween. The stripping gel 35 is preferably a thin film.

The stripping gel 35 does not cover other electrodes 31 to 33 other than the stripping electrode 34. In the case that the stripping gel 35 contacts with at least one of the other electrode 31 to 33, the stripping gel 35 would connect electrically to at least one electrode. This causes the quantification of the chemical substance to be impossible.

The inlet 36 and the air vent 38 may be disposed on the top or side plate of the cover 37. The shapes of the inlet 36 and the air vent 38 are not limited. The cover 37 covers the entire of the electrode region 30a. The cover 37 prevents the sample solution supplied therein from flowing to the connection region 30b and out of the sensor chip 300. The cover 37 is provided optionally. The sample solution may be applied to the surface of the sensor chip 300 without the cover 37.

Next, the stripping gel 35 is described below in more detail.

The stripping gel 35 contains the standard electrolyte and the ionic liquid. The ionic liquid serves as a support electrolyte. The stripping gel 35 is configured so as the standard electrolyte and the ionic liquid are not mixed with the sample solution. A method for configuring the stripping gel 35 is not limited. An example is supporting and/or including the standard electrolyte and the ionic liquid in a hydrophobic polymer. An example of the hydrophobic polymer is poly(vinylidene fluoride-hexafluoropropylene), polymethyl methacrylate, polyacrylonitrile, and polybutylacrylate.

The ionic liquid is hydrophobic. The hydrophobic ionic liquid is composed of the following cation and anion.

Cation: a cation represented by the following formula IV-(1) to IV-(6).

[Chem. 4]

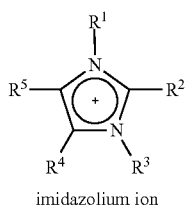

imidazolium ion    IV-(1)

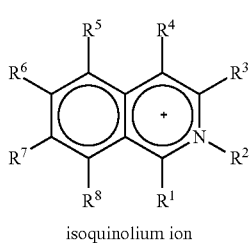

isoquinolium ion    IV-(2)

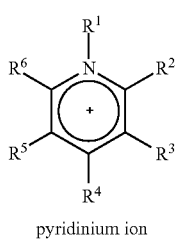

pyridinium ion    IV-(3)

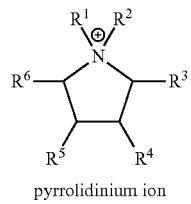

pyrrolidinium ion    IV-(4)

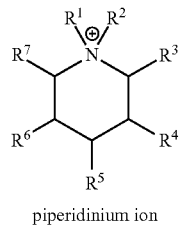

piperidinium ion    IV-(5)

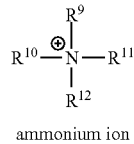

ammonium ion    IV-(6)

(wherein, $R^1$, $R^2$, $R^3$, $R^4$, $R^5$, $R^6$, $R^7$, and $R^8$ are the same as or different from each other, and represent hydrogen atom, a straight or branched alkyl group which may contain heteroatom, an aralkyl group, or an aryl group, and $R^9$, $R^{10}$, and $R^{12}$ are the same as or different from each other, and represent a straight or branched alkyl group which may contain heteroatom, an aralkyl group, or an aryl group.)

Preferably, in the imidazolium ion represented by the formula IV-(1), $R^1$ is selected from the group consisting of methyl group, ethyl group, n-propyl group, isopropyl group, n-butyl group, isobutyl group, and t-butyl group, $R^2$ is hydrogen atom or methyl group, $R^3$ is an alkyl group having carbon number of 1 to 6 which may contain hetero atom, and $R^4$ and $R^5$ are hydrogen atom.

Preferably, in the isoquinolium ion represented by the formula IV-(2), $R^2$ is an alkyl group having carbon number of 1 to 6 which may contain hetero atom, and $R^1$, $R^3$, $R^4$, $R^5$, $R^6$, $R^7$, and $R^8$ are hydrogen atom.

Preferably, in the pyridinium ion represented by the formula IV-(3), $R^1$ is an alkyl group having carbon number of 1 to 6 which may contain hetero atom, and $R^2$, $R^3$, $R^4$, $R^5$, and $R^6$ are hydrogen atoms.

Preferably, in the pyrrolidinium ion represented by the formula IV-(4), $R^1$ is selected from the group consisting of methyl group, ethyl group, n-propyl group, isopropyl group, n-butyl group, isobutyl group, and t-butyl group, $R^2$ is an alkyl group having carbon number of 1 to 6 which may contain hetero atom, $R^3$, $R^4$, $R^5$, and $R^6$ are hydrogen atom.

Preferably, in the piperidinium ion represented by the formula IV-(5), $R^1$ is selected from the group consisting of methyl group, ethyl group, n-propyl group, isopropyl group, n-butyl group, isobutyl group, and t-butyl group, $R^2$ is an alkyl group having carbon number of 1 to 6 which may contain hetero atom, and $R^3$, $R^4$, $R^5$, $R^6$, and $R^7$ are hydrogen atom.

Preferably, in the ammonium ion represented by the formula IV-(6), $R^9$, $R^{10}$, $R^{11}$, and $R^{12}$ are the same as or different from each other, and represent an alkyl group having carbon number of 1 to 6 which may contain halogen atom, a phenyl group, or a benzyl group.

Anion: an anion represented by the following formula V-(1) or V-(2).

[Chem. 5]

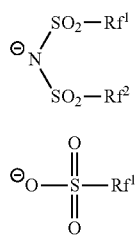

(wherein, $Rf^1$ and $Rf^2$ are the same as or different from each other, and represents a perfluoroalkyl group having carbon number of 1 to 4.)

Preferably, in the anion represented by the formula V-(1), $Rf^1$ and $Rf^2$ are identical perfluoromethyl group or perfluoroethyl group.

Preferably, in the anion represented by the formula V-(2), $Rf^1$ is trifluoromethyl group.

More specifically, the ionic liquid is exemplified below.
1,3-Dimethylimidazolium bis(trifluoromethanesulfonyl)imide,
1-Ethyl-3-methylimidazolium bis(trifluoromethanesulfonyl)imide,
1-Ethyl-3-methylimidazolium triflate,
1-Ethyl-3-methylimidazolium bis(pentafluoroethanesulfonyl)imide,
1,3-Diethylimidazolium bis(trifluoromethanesulfonyl)imide,
1,3-Diethylimidazolium triflate,
1-Butyl-3-ethylimidazolium triflate,
1,2-Dimethyl-3-ethylimidazolium bis(trifluoromethanesulfonyl)imide,
1-Butyl-3-methylimidazolium bis(trifluoromethanesulfonyl)imide,
1-Butyl-3-methylimidazolium triflate,
1-isoPropyl-3-methylimidazolium bis(trifluoromethanesulfonyl)imide,
1,2-Dimethyl-3-propyllimidazolium bis(trifluoromethanesulfonyl)imide,
N,N-Propylmethylpyrrolidinium bis(trifluoromethanesulfonyl)imide,
Propyltrimethyammonium bis(trifluoromethanesulfonyl)imide,
N,N-Methylpropylpiperidinium bis(trifluoromethanesulfonyl)imide, or
N-Butylpyridinium bis(trifluoromethanesulfonyl)imide.

The standard electrolyte is consisted of the above-mentioned anion and a metallic ion. It is preferred that the metallic ion is silver ion or copper ion (II), because it is easy to get commercially the standard electrolyte containing silver ion or copper ion (II).

It is preferred that the standard electrolyte comprises identical or similar anion to the anion which composes ionic liquid in light of solubility. The "similar anion" means any anion represented by the formula V-(1), when the anion of the ionic liquid is an anion represented by the formula V-(1). Specifically, for example, when the ionic liquid is 1-butyl-3-methylimidazolium bis(trifluoromethanesulfonyl)imide, the anion which comprises the standard electrolyte may preferably be bis(trifluoromethanesulfonyl)imide ion.

(Preparation Method of the Sensor Chip)

A procedure to prepare the sensor chip of the present embodiment is described below.

(Formation of Electrodes)

An insulated substrate coated by a photoresist is exposed to an ultraviolet through a mask for patterning, followed by alkaline developing. A metal is sputtered on the patterned substrate 30. The residue photoresist is dissolved into an organic solvent to remove the unnecessary metal. The whole surface of the substrate 30 is coated by an insulating film. The insulating film over the electrodes is removed by dry etching to form the pair of comb-shaped electrodes 31a/31b, the reference electrode 32, the counter electrode 33 and the stripping electrode 34. The Ag/AgCl electrode is formed by applying an Ag/AgCl paste on the reference electrode 32.

(Formation of Stripping Gel 35)

The stripping gel 35 may be formed as below.

First, poly(vinylidene fluoride-hexafluoropropylene) is dissolved in acetone by ultrasonic wave on ice cooling to prepare an acetone solution. 1-Butyl-3-methylimidazolium bis(trifluoromethanesulfonyl)imide containing silver bis(trifluoromethanesulfonyl)imide is added to the acetone solution. Subsequently, the acetone solution is stirred and dropped on the stripping electrode 34. Finally, the acetone is evaporated to form the stripping gel 35.

(Step (b))

A sample solution is supplied to the surface of the above-mentioned sensor chip 300 to cover the surface with the sample solution.

The sample solution contains a chemical substance to be quantified according to the present invention. An example of the chemical substance is an antigen, an antibody, a nucleic acid, a cell, bacteria, virus, a hapten, and sugar.

Preferably, the cover 37 is provided with the sensor chip 300. The sample solution supplied through the inlet 36 covers the surface of the electrode region 30a of the sensor chip 300. The air in the space between the cover 37 and the sensor chip 300 is drained through the air vent 38.

More preferably, the space between the cover 37 and the sensor chip 300 is filled with the sample solution. This allows the volume of the liquid solution to be constant.

The sample solution contains a chemical substance to be quantified and an oxidation-reduction substance. In the present invention, the sample solution contains the oxidation-reduction substance in the oxidation condition. The chemical substance to be quantified and an oxidation-reduction substance may be distinct. For example, the chemical substance to be quantified is an enzyme, and the oxidation-reduction substance is an electric mediator such as potassium ferricyanide and rutheniumhexaammine. Or, the chemical substance to be quantified may be modified with the oxidation-reduction substance.

The substitutional stripping voltammetry comprises a step (c) and a step (d).

(Step (c))

In the step (c), the switch 41a and the switch 41b are connected to the respective terminals A, and a constant potential is applied to the first working electrode 31a. Furthermore, the second working electrode 31b is electrically connected to the stripping electrode 34 to form a redox cycle between the pair of comb-shaped electrodes 31a/31b.

When the oxidation-reduction substance and the standard electrolyte are potassium ferricyanide and silver bis(trifluoromethanesulfonyl)imide, respectively, the following reactions represented by the following chemical formulas (VI) to (VIII) are caused on the comb-shaped electrodes 31a, the comb-shaped electrodes 31b, and the stripping electrode 34.

Comb-Shaped Working Electrode 31a:

[Chem. 6]

$$[Fe(CN)_6]^{3\ominus} + e^{\ominus} \longrightarrow [Fe(CN)_6]^{4\ominus} \quad \text{(VI)}$$
$$\text{(oxidant)} \quad\quad\quad\quad \text{(reductant)}$$

Comb-Shaped Working Electrode 31b:

[Chem. 7]

$$[Fe(CN)_6]^{4\ominus} \longrightarrow [Fe(CN)_6]^{3\ominus} + e^{\ominus} \quad \text{(VII)}$$
$$\text{(reductant)} \quad\quad\quad \text{(oxidant)}$$

Stripping Electrode 34:

[Chem. 8]

$$Ag^{\oplus} + e^{\ominus} \rightarrow Ag\downarrow \quad \text{(VIII)}$$

Silver is deposited on the surface of the stripping electrode 34, which is composed of gold, platinum or glassy carbon.

(Step (d))

In the step (d), the switch 41a and the switch 41b are connected to the respective terminals B. No potential is applied to either the first working electrode 31a or the second working electrode 31b. The stripping electrode 34 is swept with the potentiostat 42 to cause the silver, which has been deposited, to be dissolved in the stripping gel as shown in the following chemical formula (IX).

Stripping Electrode 34:

[Chem. 9]

$$Ag \rightarrow Ag^{\oplus} + e^{\ominus} \quad \text{(IX)}$$

If the stripping gel 35 contains water, the water inhibits the reaction represented by the formula (VIII). Because water has an affinity with the silver ion. Therefore, the stripping gel 35 contains no water. However, the stripping gel may contain water as long as the content of the water is within a range of a determination precision is not adversely affected. The ionic liquid is nonvolatile. Accordingly, unlike prior arts, the evaporation of the stripping gel 35 is suppressed in the step (c) and in the step (d). This allows the concentration of the standard electrolyte to be maintained. As a result, the quantification of the chemical substance is allowed to be more accurate. This characterizes the present invention.

In the longer period the constant potential is applied in the step (c), the higher sensitivity is achieved, since the deposition amount of silver is increased.

The amount of the current flowing on the dissolution in the step (d) is proportional to the deposited amount of the silver. The deposited amount of the silver is proportional to the product of the concentration of the oxidation-reduction substance (oxidant) by the period when the potential is applied in the step (c). Namely, the following equation is satisfied.

[Math. 1]

(the deposition amount of the silver) = (the concentration of the oxidation-reduction substance (oxidant))) × (the period when the potential is applied in the step (c))

Accordingly, the concentration of the oxidation-reduction substance (oxidant) is calculated from the amount of the current flowing in the step (d). The chemical substance is quantified on the basis of the concentration of the oxidation-reduction substance (oxidant). Needless to say, similarly to a typical procedure, when the chemical substance is quantified from the current, a standard curve which has been prepared is used.

INDUSTRIAL APPLICABILITY

The present invention provides a method for quantifying a chemical substance with high accuracy using substitutional stripping voltammetry and a sensor chip used therefor.

| REFERENCE SIGNS LIST | |
|---|---|
| 300 | sensor chip |
| 30 | substrate |
| 30a | electrode region |
| 30b | connection region |
| 31a | first working electrode |
| 31b | second working electrode |
| 32 | reference electrode |
| 33 | counter electrode |
| 34 | stripping electrode |
| 35 | stripping gel |
| 36 | inlet |
| 37 | cover |
| 38 | air vent |
| 39 | lead wire |
| 41 | switch box |
| 41a | switch |
| 41b | switch |
| 42 | potentiostat |
| W | working electrode of potentiostat |
| R | reference electrode of potentiostat |
| C | counter electrode of potentiostat |

What is claimed is:

1. A method for quantifying a chemical substance contained in a sample solution, the method comprising:

a step (a) of preparing a sensor chip, wherein:
the sensor chip comprises a substrate, a pair of working electrodes, a counter electrode, a stripping electrode, and a stripping gel,
the pair of working electrodes is composed of a first working electrode and a second working electrode,
a surface of the stripping electrode comprises gold, platinum, or glassy carbon,
the stripping gel covers the stripping electrode,
the stripping gel does not cover the pair of the working electrodes or the counter electrode,
the stripping gel contains a standard electrolyte and an ionic liquid,
the stripping gel contains no water,
the ionic liquid is hydrophobic and nonvolatile,
the ionic liquid includes a cation and an anion,
the standard electrolyte includes the anion and a metallic ion;

a step (b) of supplying the sample solution to a surface of the sensor chip to cover the surface of the sensor chip with the sample solution, wherein the sample solution contains the chemical substance and an oxidation-reduction substance or contains the chemical substance modified with an oxidation-reduction substance;

a step (c) of applying a potential to the first working electrode with potentiostat, and connecting the second working electrode to the stripping electrode to generate reactions represented by the following formulas (I) to (III) in surfaces of the first working electrode, the second working electrode, and the stripping electrode, respectively, the first working electrode:

[Chem. 1]

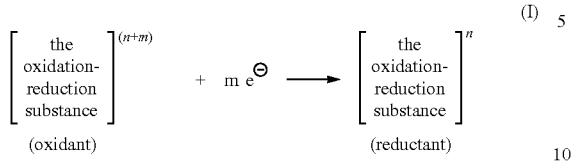

(I)

wherein, n represents an integer, and m represents a positive integer, the second working electrode:

[Chem. 2]

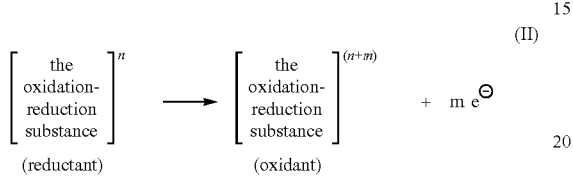

(II)

wherein, n represents an integer, and m represents a positive integer, and the stripping electrode:

[Chem. 3]

(III)

wherein, M represents a metallic element, and s represents a positive integer, and the metallic element is deposited on the surface of the stripping electrode;
a step (d) of applying a potential to the stripping electrode in a condition where no potential is applied to either the first working electrode or the second working electrode to measure a current flowing through the stripping electrode; and
a step (e) of calculating concentration of the oxidation-reduction substance as an oxidant to quantify the chemical substance on the basis of the calculated concentration.

2. The method according to claim 1, wherein:
the sensor chip further comprises a cover with an inlet,
a space is formed between the cover and the sensor chip, and
in the step (b), the sample solution is supplied through the inlet to the surface of the sensor chip.

3. The method according to claim 2, wherein:
the sensor chip further comprises an air vent, and
in the step (b), the air which has filled the space is drained through the air vent.

4. The method according to claim 2, wherein, after the step (b), the space is filled with the sample solution.

5. The method according to claim 1, wherein
the cation and the anion are selected from the following groups (I) and (II), respectively:

Group (I): a cation represented by the following formula IV-(1) to IV-(6):

[Chem. 4]

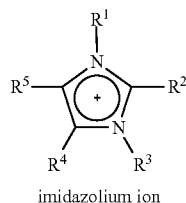

imidazolium ion

IV-(1)

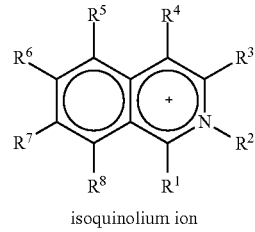

isoquinolium ion

IV-(2)

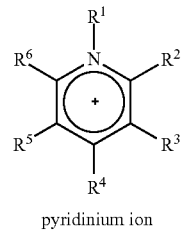

pyridinium ion

IV-(3)

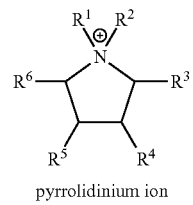

pyrrolidinium ion

IV-(4)

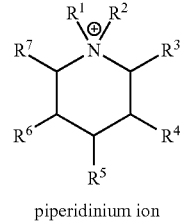

piperidinium ion

IV-(5)

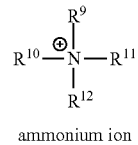

ammonium ion

IV-(6)

wherein, $R^1$, $R^2$, $R^3$, $R^4$, $R^5$, $R^6$, $R^7$, and $R^8$ are the same as or different from each other, and represent hydrogen atom, a straight or branched alkyl group which may contain heteroatom, an aralkyl group, or an aryl group, and $R^9$, $R^{10}$, $R^{11}$, and $R^{12}$ are the same as or different from each other, and represent a straight or branched alkyl group which may contain heteroatom, an aralkyl group, or an aryl group; and Group (II): an anion represented by the following formula V-(1) or V-(2):

[Chem. 5]

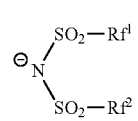

V-(1)

-continued

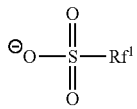

V-(2)

wherein, $R^{f1}$ and $R^{f2}$ are the same as or different from each other, and represent a perfluoroalkyl group having carbon number of 1 to 4.

6. The method according to claim 1, wherein
the ionic liquid is at least one selected from the group consisting of:
1,3-Dimethylimidazolium bis(trifluoromethanesulfonyl)imide,
1-Ethyl-3-methylimidazolium bis(trifluoromethanesulfonyl)imide,
1-Ethyl-3-methylimidazolium triflate, 1-Ethyl-3-methylimidazolium bis(pentafluoroethanesulfonyl)imide,
1,3-Diethylimidazolium bis(trifluoromethanesulfonyl)imide,
1,3-Diethylimidazolium triflate,
1-Butyl-3-ethylimidazolium triflate,
1,2-Dimethyl-3-ethylimidazolium bis(trifluoromethanesulfonyl)imide,
1-Butyl-3-methylimidazolium bis(trifluoromethanesulfonyl)imide,
1-Butyl-3-methylimidazolium triflate,
1-isoPropyl-3-methylimidazolium bis(trifluoromethanesulfonyl)imide,
1,2-Dimethyl-3-propyllimidazolium bis(trifluoromethanesulfonyl)imide,
N,N-propylmethylpyrrolidinium bis(trifluoromethanesulfonyl)imide,
Propyltrimethyammonium bis(trifluoromethanesulfonyl)imide,
N,N-methylpropylpiperidinium bis(trifluoromethanesulfonyl)imide, and
N-butylpyridinium bis(trifluoromethanesulfonyl)imide.

7. The method according to claim 1, wherein the metallic ion is silver ion or copper ion (II).

8. A sensor chip for a substitutional stripping voltammetry, comprising:
a substrate;
a pair of working electrodes;
a counter electrode;
a stripping electrode; and
a stripping gel, wherein:
the pair of working electrodes is composed of a first working electrode and a second working electrode,
the surface of the stripping electrode comprises gold, platinum, or glassy carbon,
the stripping gel covers the stripping electrode,
the stripping gel does not cover the pair of the working electrodes or the counter electrode,
the stripping gel contains a standard electrolyte and an ionic liquid,
the ionic liquid is hydrophobic,
the ionic liquid includes a cation and an anion, and
the standard electrolyte includes the anion and a metallic ion.

9. The sensor chip according to claim 8, wherein:
the sensor chip further comprises a cover with an inlet, and
a space is formed between the cover and the sensor chip.

10. The sensor chip according to claim 9, wherein, the sensor chip further comprises an air vent.

11. The sensor chip according to claim 8, wherein:
the cation and the anion are selected from the following groups (I) and (II), respectively:
Group (I): a cation represented by the following formula IV-(1) to IV-(6):

[Chem. 4]

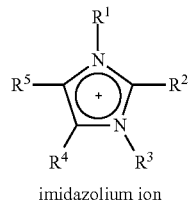

IV-(1)

imidazolium ion

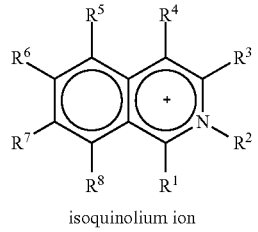

IV-(2)

isoquinolium ion

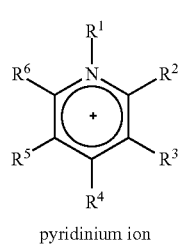

IV-(3)

pyridinium ion

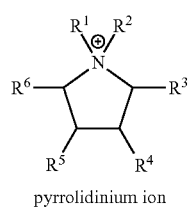

IV-(4)

pyrrolidinium ion

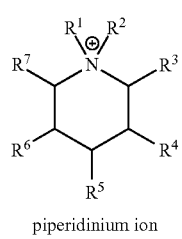

IV-(5)

piperidinium ion

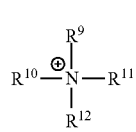

IV-(6)

ammonium ion wherein, $R^1$, $R^2$, $R^3$, $R^4$, $R^5$, $R^6$, $R^7$, and $R^8$ are the same as or different from each other, and represent hydrogen atom, a straight or branched alkyl group which may contain heteroatom, an aralkyl group, or an aryl group, and $R^9$, $R^{10}$, $R^{11}$, and $R^{12}$ are the same as or different from each other, and represent a straight or branched alkyl group which may contain heteroatom, an aralkyl group, or an aryl group; and Group (II): an anion represented by the following formula V-(1) or V-(2):

[Chem. 5]

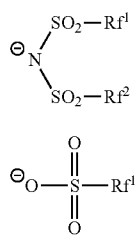

wherein, $R^{f1}$ and $R^{f2}$ are the same as or different from each other, and represent a perfluoroalkyl group having carbon number of 1 to 4.

12. The sensor chip according to claim 8, wherein the ionic liquid is at least one selected from the group consisting of:

1,3-Dimethylimidazolium bis(trifluoromethanesulfonyl)imide,
1-Ethyl-3-methylimidazolium bis(trifluoromethanesulfonyl)imide,
1-Ethyl-3-methylimidazolium triflate, 1-Ethyl-3-methylimidazolium bis(pentafluoroethanesulfonyl)imide,
1,3-Diethylimidazolium bis(trifluoromethanesulfonyl)imide,
1,3-Diethylimidazolium triflate,
1-Butyl-3-ethylimidazolium triflate,
1,2-Dimethyl-3-ethylimidazolium bis(trifluoromethanesulfonyl)imide,
1-Butyl-3-methylimidazolium bis(trifluoromethanesulfonyl)imide,
1-Butyl-3-methylimidazolium triflate,
1-isoPropyl-3-methylimidazolium bis(trifluoromethanesulfonyl)imide,
1,2-Dimethyl-3-propyllimidazolium bis(trifluoromethanesulfonyl)imide,
N,N-propylmethylpyrrolidinium bis(trifluoromethanesulfonyl)imide,
Propyltrimethyammonium bis(trifluoromethanesulfonyl)imide,
N,N-methylpropylpiperidinium bis(trifluoromethanesulfonyl)imide, and
N-butylpyridinium bis(trifluoromethanesulfonyl)imide.

13. The sensor chip according to claim 8, wherein the metallic ion is silver ion or copper ion (II).

* * * * *